United States Patent
Lee

(10) Patent No.: US 10,349,989 B2
(45) Date of Patent: Jul. 16, 2019

(54) BONE FRAGMENT-FIXING DEVICE AND DRILL ASSEMBLY FOR CUTTING BONE FRAGMENT

(71) Applicant: UNIVERSITY-INDUSTRY COOPERATION GROUP OF KYUNG HEE UNIVERSITY, Gyeonggi-do (KR)

(72) Inventor: Deok Won Lee, Seoul (KR)

(73) Assignee: UNIVERSITY-INDUSTRY COOPERATION GROUP OF KYUNG HEE UNIVERSITY, Gyeonggi-Do (KR)

( * ) Notice: Subject to any disclaimer, the term of this patent is extended or adjusted under 35 U.S.C. 154(b) by 268 days.

(21) Appl. No.: 15/108,003

(22) PCT Filed: Jun. 26, 2014

(86) PCT No.: PCT/KR2014/005684
§ 371 (c)(1),
(2) Date: Jun. 24, 2016

(87) PCT Pub. No.: WO2015/099254
PCT Pub. Date: Jul. 2, 2015

(65) Prior Publication Data
US 2016/0324556 A1    Nov. 10, 2016

(30) Foreign Application Priority Data
Dec. 27, 2013 (KR) .......................... 10-2013-0165646

(51) Int. Cl.
*A61B 17/80* (2006.01)
*A61B 17/16* (2006.01)

(52) U.S. Cl.
CPC ...... *A61B 17/8071* (2013.01); *A61B 17/1637* (2013.01)

(58) Field of Classification Search
CPC .. A61B 17/686; A61B 17/688; A61B 17/8071
See application file for complete search history.

(56) References Cited

U.S. PATENT DOCUMENTS 5,503,164 A * 4/1996 Friedman ........... A61B 17/8085
128/897
6,302,884 B1 * 10/2001 Wellisz ................ A61B 17/688
606/281

(Continued)

FOREIGN PATENT DOCUMENTS

KR   20130004370   7/2013

OTHER PUBLICATIONS

Lee, "Genioglossus muscle advancement techniques for obstructive sleep apnea", Oral and Maxillofacial Surgery Clinics of North America, 2002, pp. 377-384.

(Continued)

*Primary Examiner* — Nicholas W Woodall
(74) *Attorney, Agent, or Firm* — Workman Nydegger

(57) ABSTRACT

A bone fragment-fixing device of the present invention including: a supporting portion for supporting, on an inner side of a mandible, a bone fragment generated by cutting the mandible; a connecting portion which is connected to one side of the supporting portion and protrudes to a height corresponding to the outer side of the mandible along the cut surface of the bone fragment; and a fixing portion connected to the connecting portion and formed in a shape corresponding to the mandible around the bone fragment.

7 Claims, 7 Drawing Sheets

(56) References Cited

U.S. PATENT DOCUMENTS

| | | | | |
|---|---|---|---|---|
| 6,767,369 | B2* | 7/2004 | Boyer, II | B29C 43/006 |
| | | | | 623/23.63 |
| 7,833,253 | B2* | 11/2010 | Ralph | A61B 17/688 |
| | | | | 403/397 |
| 8,986,394 | B2* | 3/2015 | Liao | A61F 2/2875 |
| | | | | 623/23.72 |
| 9,777,492 | B2* | 10/2017 | Freeman | E04G 23/0203 |
| 2005/0107813 | A1* | 5/2005 | Gilete Garcia | A61B 17/68 |
| | | | | 606/151 |

OTHER PUBLICATIONS

Lewis et al., "Genioglossus muscle advancement with genioglossus bone advancement technique for base of tongue obstruction", Journal of Otolaryngology, vol. 32, No. 3, 2003, pp. 168-173.

Li et al., "Obstructive Sleep Apnea Surgery: Genioglossus Advancement Revisited", Journal of Oral and Maxillofacial Surgery, 2001, pp. 1181-1184.

Waite et al., "The stability of maxillary advancement using Le Fort I osteotomy with and without genial bone grafting", International Jourdan of Oral and Maxillofacial Surgery, 1996, pp. 1-3.

* cited by examiner

[Fig. 1]
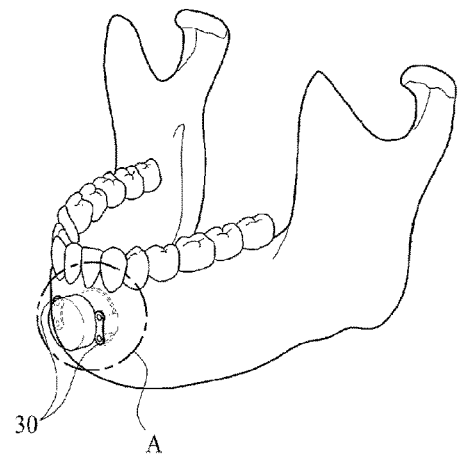
[Fig. 2]
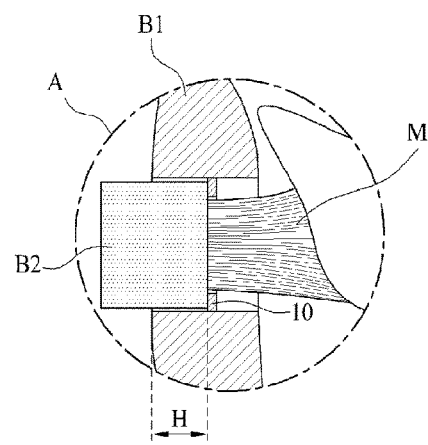
[Fig. 3]
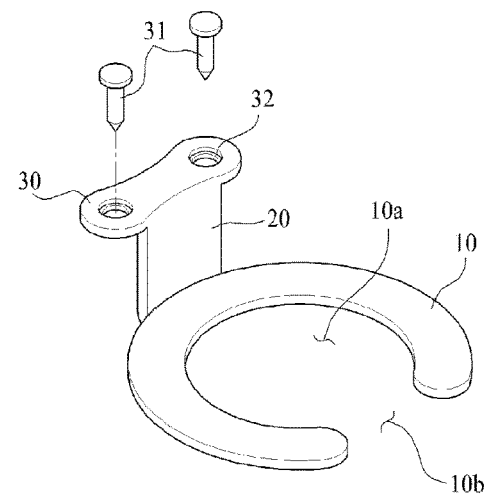

[Fig. 4]
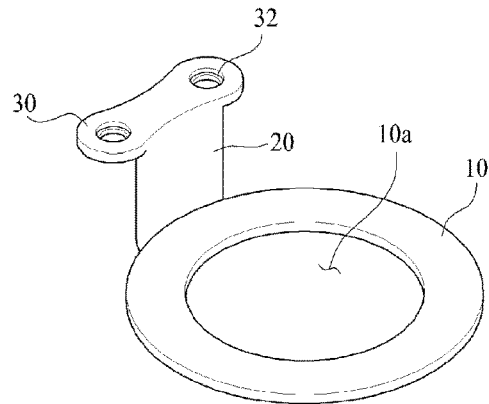
[Fig. 5]
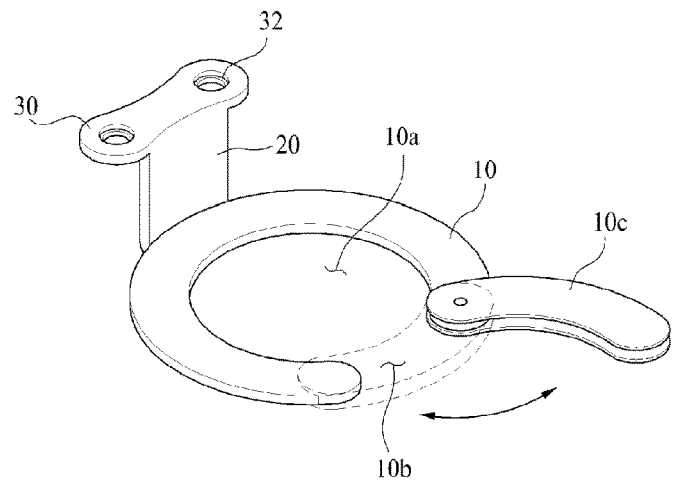
[Fig. 6]
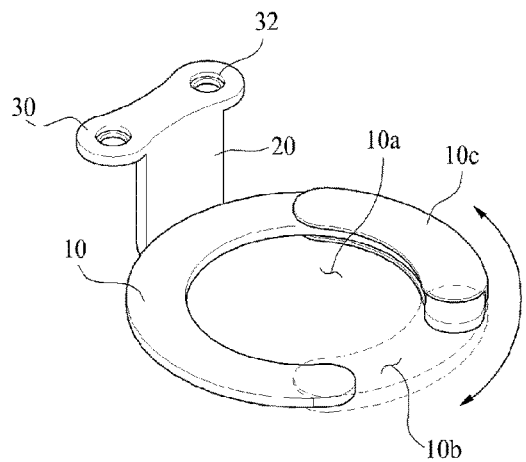

[Fig. 7]
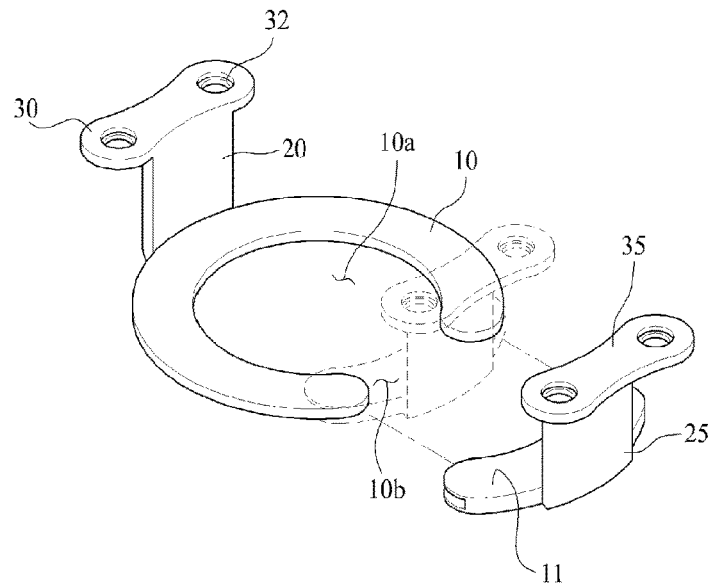
[Fig. 8]
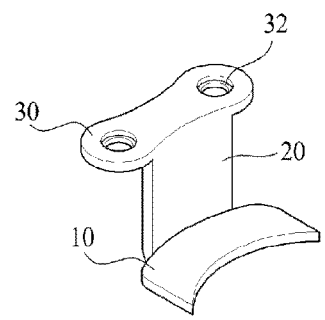
[Fig. 9]
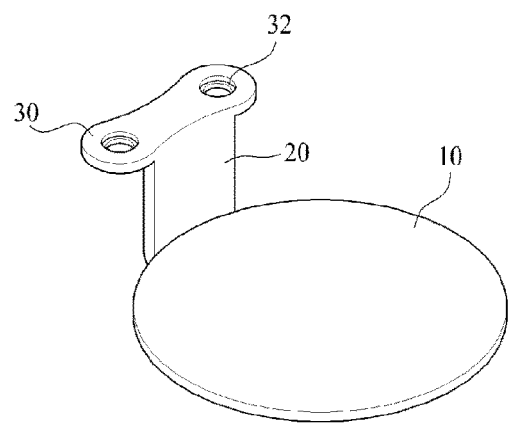

[Fig. 10]
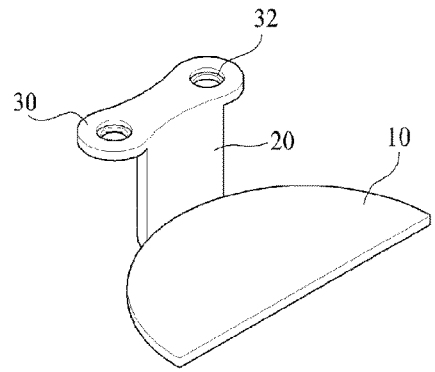
[Fig. 11]
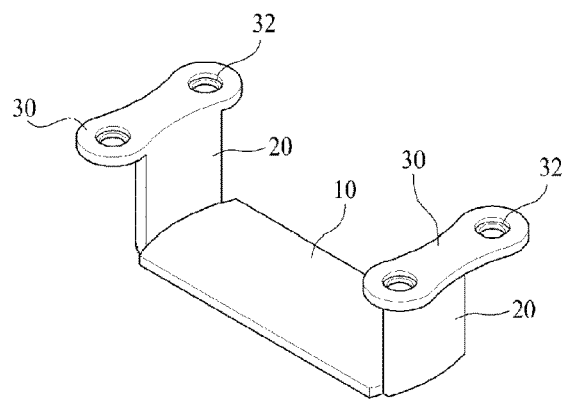
[Fig. 12]
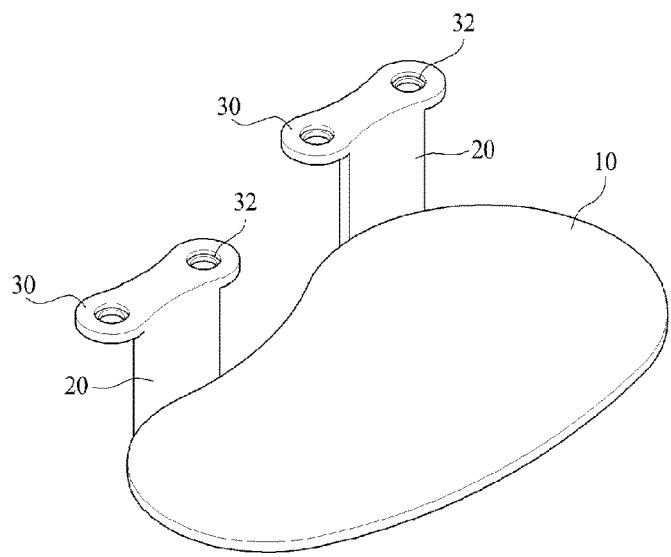

[Fig. 13]
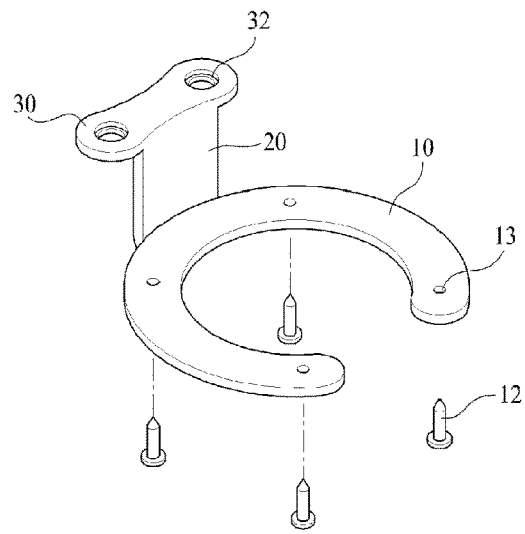
[Fig. 14]
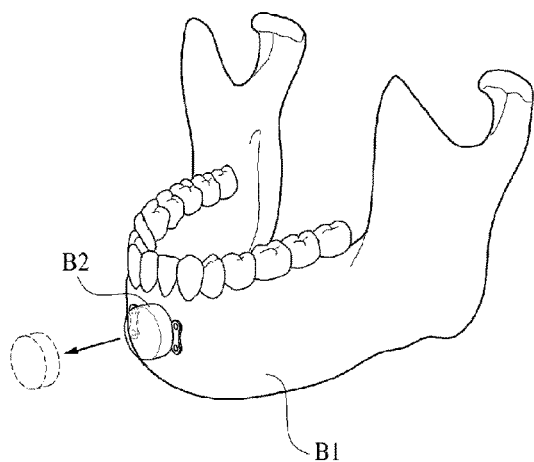
[Fig. 15]
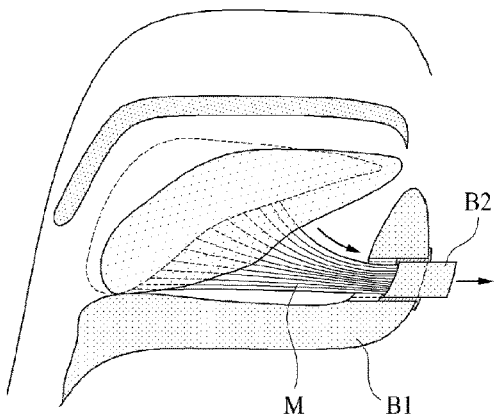

[Fig. 16]
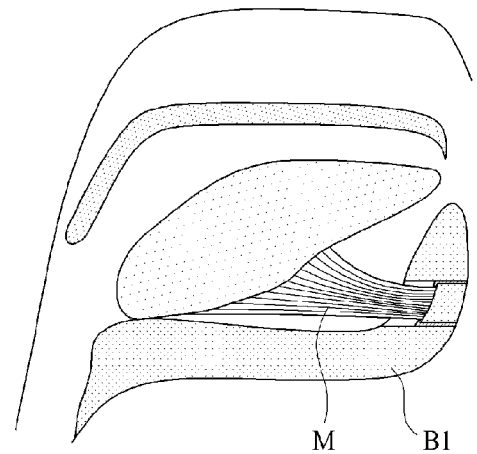
M  B1
[Fig. 17]
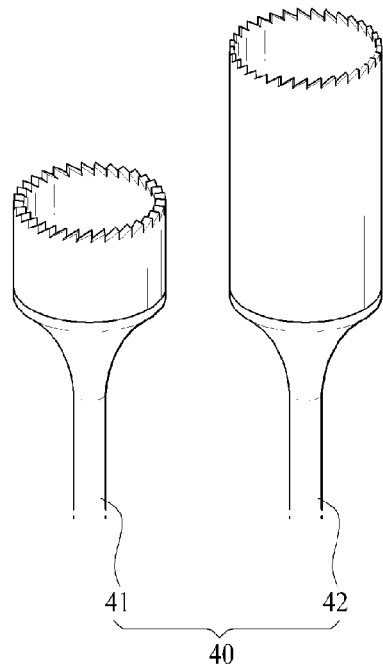
41  42
40

[Fig. 18]
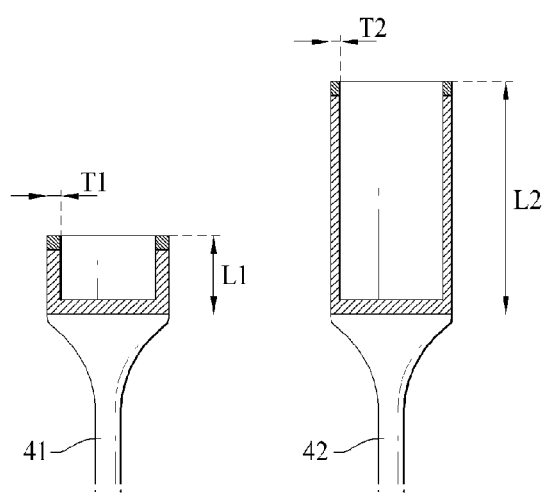

BONE FRAGMENT-FIXING DEVICE AND DRILL ASSEMBLY FOR CUTTING BONE FRAGMENT

TECHNICAL FIELD

The present invention relates to a bone fragment-fixing device and a drill assembly for cutting bone fragment, and more particularly, to a bone fragment-fixing device that is capable of more stably supporting the bone fragments by including a fixing portion, a supporting portion and a connecting portion and by supporting the bone fragments on an inner side surface, and a drill assembly that reduces frictional heat generated when cutting the bone fragments.

BACKGROUND ART

Generally, when a fracture occurs, fracture-treating methods of using a bone fixing member to treat the fracture are often operated. In particular, in the case of correction and surgical operation of a mandible, methods of fixing separated bones of a mandible using bolts and a fixing plate are often used.

Such a treatment is mainly used in a double jaw surgery for the treatment of malocclusion of the teeth, a genioplasty for the treatment of lantern jaw and the like. In particular, a genioglossus muscle advancement surgery for snoring surgery is a method of pull the genioglossus muscle fixed to the inside surface of the mandible and expanding the airway to prevent the snoring. More specifically, a method of fixing the bone fragments using the fixing member, after pulling the bone fragments generated by partially cutting the mandible connected to the genioglossus muscle to the outside is used.

The general fixing method of the fixing member is described in published utility model No. 20-2013-0004370 (Jan. 5, 2012). Because the general fixing method of the fixing member couples both bones needed to be fixed from the outer surface, the support is not stable. Further, there is a problem that, since a force of fixing a site directly coupled to the bone fragments with screws, the bone fragments are strained.

Also, there is a problem that, because fixation is performed on all of the original bone and bone fragments in the treatment, there are many treatment steps, a surgical time becomes longer, and the burden applied to the patient also increases accordingly.

Further, there is a problem that, as the bone fragments are fixed by advancing outward, the bone fragments protrude outward, which may cause inconveniences in beauty and the daily life of patients after treatment.

Further, there is a problem that a lot of frictional heat occurs, by friction between the blade and the mandible when cutting some of t the part of the mandible.

DISCLOSURE

Technical Problem

An aspect of the present invention provides a bone fragment-fixing device and a drill assembly that can reduce a frictional heat, stably support the bone fragments, simplify the surgical process to save time and money, reduce the burden on the patient, and improve beauty and the discomfort of the patient, when cutting the bone fragments, using a bone fragment-fixing device including a fixing portion, a supporting portion and a connecting portion, and a drill apply a two-stage blade.

Technical Solution

According to an aspect of the present invention, there is provided a bone fragment-fixing device which includes a supporting portion for supporting, on an inner side of a mandible, a bone fragment generated by cutting the mandible; a connecting portion which is connected to one side of the supporting portion and protrudes to a height corresponding to the outer side of the mandible along the cut surface of the bone fragment; and a fixing portion connected to the connecting portion and formed in a shape corresponding to the mandible around the bone fragment.

Further, the genioglossus muscle is connected to the inner surface of the bone fragment, and the supporting part may be formed to support the inner surface of the bone fragment, without interfering with the genioglossus muscle.

At this time, the supporting portion may be formed with a housing portion in which the genioglossus muscle is housed.

Further, the supporting portion may be further formed with an inducing portion which induces the genioglossus muscle to be housed in the housing portion.

Further, the supporting portion may further include a switching portion which opens and closes the inducing portion.

Otherwise, the device may include a switching member that includes an auxiliary supporting portion located in the inducing portion, the connecting portion and the fixing portion.

Further, the supporting portion may be formed to include a fixing member for being fastened to the bone fragment.

Further, the supporting portion may be formed in an area smaller than an area of the bone fragments generated by cutting of the mandible.

Meanwhile, the drill assembly for cutting the bone fragment includes a first blade and a second blade, the first blade being detachably connected to a drill, being formed so that a blade for cutting the mandible by rotation is arranged in a circular form, and the blade having a length smaller than the thickness of the mandible, and the second saw bale being detachably connected to the drill, being formed so that a blade for cutting the mandible by rotation is disposed in a circular form, an outer diameter of the blade being the same as an outer diameter of the first blade and being relatively thinner than the thickness of the first blade, and a length of the blade being formed longer than the thickness of the mandible.

Advantageous Effects

According to an aspect of the present invention, the bone fragments-fixing device and the drill assembly of the present invention having the aforementioned configuration have the following effects.

First, by supporting and fixing the bone fragments on the inner surface, as compared to the prior art, there are effects that the bone fragments are more stably fixed, the force applied directly to the bone fragments through the fixing member is reduced, and the bone fragments are not strained.

Second, there are effects that the use of the fixing member is reduced when performing the surgical operation, and the treatment steps can be reduced through reduction in time and effort for artificially moving the position of the bone fragments. Thus, there are effects that the treatment process is simplified, the treatment time and effort can be saved, and the patient's burden can be reduced accordingly.

Third, when the bone fragments are fixed by being pulled in an outward direction of the mandible, because the bone fragment-fixing device supports and fixes the bone fragments on the inner surface, the protruding portion that protrudes to the outside of the mandible can be cut. As a result, there is an effect that it is possible to prevent the beauty problem occurred after the surgery or inconveniences that may occur in daily life of the patient in advance.

Fourth, there is an effect that the frictional heat generated between the blade and the mandible when cutting the bone fragments is reduced, and a burden applied to the patient is reduced.

The effects of the present invention are not limited to the foregoing effects, and other effects that have not been mentioned will be clearly understood to those skilled in the art from the scope of the claims.

DESCRIPTION OF DRAWINGS

FIG. 1 is a diagram illustrating a surgical embodiment of genioglossus muscle advancement surgery using a bone fragment-fixing device according to the present invention.

FIG. 2 is a cross-sectional view of a surgical embodiment of the genioglossus muscle advancement surgery using the bone fragment-fixing device according to the present invention.

FIG. 3 is a perspective view illustrating an overall configuration of the bone fragment-fixing device according to the first embodiment of the present invention.

FIG. 4 is a perspective view illustrating a configuration of a second embodiment that maximizes the support performance of the supporting portion.

FIG. 5 is a perspective view illustrating a configuration of a third embodiment in which a switching portion is formed in the inducing portion of the supporting portion.

FIG. 6 is a perspective view illustrating a configuration of a fourth embodiment to which another embodiment of the switching portion is applied.

FIG. 7 is a perspective view illustrating a configuration of a fifth embodiment in which the switching portion is formed on the inducing portion of the supporting portion.

FIG. 8 is a perspective view illustrating a sixth embodiment in which the supporting portion is modified.

FIG. 9 is a perspective view illustrating an overall configuration of a bone fragment-fixing device according to a seventh embodiment of the present invention.

FIG. 10 is a perspective view illustrating a configuration of an eighth embodiment in which the supporting portion supports and fixes some of the bone fragments.

FIG. 11 is a perspective view illustrating a configuration of a ninth embodiment in which the bone fragment-fixing device includes a plurality of connecting portions and fixing portions.

FIG. 12 is a perspective view illustrating a modified embodiment of a ninth embodiment.

FIG. 13 is a perspective view illustrating a configuration of a tenth embodiment in which the supporting portion includes a fixing member for being fastened to the bone fragment.

FIG. 14 is a diagram illustrating the cutting of bone fragments after performing the genioglossus muscle advancement surgery using the bone fragment-fixing device according to an embodiment of the present invention.

FIG. 15 is a cross-sectional view illustrating a state in which the genioglossus muscle is pulled by treatment of the genioglossus muscle advancement surgery using bone fragment-fixing device according to an embodiment of the present invention.

FIG. 16 is a cross-sectional view illustrating a state of cutting the bone fragments protruding after performing the treatment the genioglossus muscle advancement surgery using the bone fragment-fixing device according to an embodiment of the present invention.

FIG. 17 is a diagram illustrating the assembly of a drill for cutting the bone fragments according to the present invention.

FIG. 18 is a diagram illustrating the cross-section of the drill assembly for cutting the bone fragments according to the present invention.

DESCRIPTION OF REFERENCE NUMERALS

10: supporting portion
10a: housing portion
10b: inducing portion
10c: switching portion
11: switching portion
12: bolt
13: coupling hole
20: connecting portion
30: fixing portion
31: bolt
32: coupling hole
40: drill assembly
41: first blade
42: second blade
L1: length of first blade
L2: length of second blade
T1: thickness of first blade
T2: thickness of second blade
B1: mandible
B2: bone fragments
M: genioglossus muscle
H: distance between inside of bone fragment and outside of mandible

BEST MODE

Hereinafter, embodiments of the invention will be described in detail with reference to the accompanying drawings. The drawings are attached hereto to help explain exemplary embodiments of the invention, and the present invention is not limited to the drawings and embodiments. In the drawings, some elements may be exaggerated, reduced in size, or omitted for clarity or conciseness.

Hereinafter, preferred embodiments of the present invention capable of specifically achieving an object of the present invention will be described with reference to the accompanying drawings. In describing the present embodiment, the same components will be denoted by the same names and same reference numerals, and additional description thereof will not be provided.

FIG. 1 is a diagram illustrating a surgical embodiment of genioglossus muscle advancement surgery using a bone fragment-fixing device according to the present invention, and FIG. 2 is a cross-sectional view of a surgical embodiment of the genioglossus muscle advancement surgery sing the bone fragment-fixing device according to the present invention.

The bone fragment-fixing device of the present invention can be universally used in treatment for fixing the bone fragments that are generated by the fracture or cutting of a mandible B1. However, in order to more clearly explain the present invention, as a main embodiment, the description will be given of a case where the device is applied to the genioglossus muscle advancement surgery, and in particular, as shown in FIGS. 1 and 2, a treatment in which a bone fragment B1 generated by cutting some of the mandible B1, to the inside of which the genioglossus muscle M is connected, is advanced to the outside of the B1 pull to pull the genioglossus muscle M, thereby more widely ensuring the airway and improving the symptoms of snoring.

Configuration of Bone Fragment-Fixing Device

First Embodiment

FIG. 3 is a perspective view illustrating an overall configuration of the bone fragment-fixing device according to the first embodiment of the present invention.

The fixing device of the present invention is a device for fixing the bone fragment B2, generated by being cut by the fracture or medical purposes, with the original bone, by supporting the bone fragment from the rear surface.

The bone fragment-fixing device of the present invention, as shown in FIG. 3, is broadly made up of supporting portion 10, a connecting portion 20 and a fixing portion 30.

The supporting portion 10 is a device for fixing the inner surface of the bone fragment B2 while supporting. The supporting portion 10 is made up of a plate member generally corresponding to the bone fragment B2, and a housing portion 10a penetrated so that the genioglossus muscle M can be inserted is formed on a center one side in order to prevent an occurrence of interference with the genioglossus muscle M connected to the bone fragment B2.

The supporting portion 10 is made up of a ring-shaped member including the housing portion 10a which can house the genioglossus muscle M, without causing the interference with the genioglossus muscle M connected to the bone fragment B2, while supporting some of the inner surface of the bone fragment B2. The housing portion 10a is formed in the form of preventing the supporting portion 10 from interfering with the genioglossus muscle M. At this time, the shape of the housing portion 10a may be configured in any shape as long as the shape does not strain or damage the genioglossus muscle M. However, it is preferably formed in a circular shape.

Further, because the supporting portion 10 is in direct contact with the genioglossus muscle M through the housing portion 10a, it is advantageous to use a material that is harmless for the human body, without causing a burden on genioglossus muscle M.

Further, the supporting portion 10 is formed with an inducing portion 10b which allows the genioglossus muscle M to be inserted into the housing portion 10a. The inducing portion 10b means a portion that opens a part of the supporting portion 10 to be able to house the genioglossus muscle M in the housing portion 10a, when coupling the supporting portion 10 with the inner surface of the bone fragment B2 to support the bone fragment B2 connected to the genioglossus muscle M.

The connecting portions 20 is a device for connecting the supporting portion 10 with the fixing portion 30 to be described later.

The connecting portion 20 is formed on one side of the frame portion of the supporting portion 10 to protrude along the outer peripheral surface of the bone fragment B2. At least one or more connecting portions 20 may be formed on one side of the frame portion of the supporting portion 10. If a plurality of connecting portions 20 are formed, each of the connecting portions 20 may be provided at equal intervals.

The connecting portion 20 may have a length H corresponding to a length from the inner surface of the pulled mandible B1 to the outer surface of the bone fragment B2.

The fixing portion 30 is provided at the other side terminal end of the connecting portion 20 connected to the supporting portion 10 so as to be bent in one direction. At this time, the fixing portion 30 is bent outward so as to be fixed to the outer peripheral surface of the mandible B1 adjacent to the bone fragment B2.

The fixing portion 30 is made up of a plate corresponding to the outer surface shape of the mandible B1 around the bone fragment, and coupling holes 32 for being coupled with bolts are formed at one side. Such a fixing portion 30 is fixed to the mandible B1 through the fixing member such as the bolts 31 passing through the coupling holes 32.

At this time, the material of the bolts 31 may be made of titanium or various alloys since the bolts are used as a medical purpose.

In this embodiment, although the mandible B1 and the bone fragment-fixing device of the present invention are coupled to each other through the bolts 31 and the coupling holes 32, various coupling forms are applicable as long as they are included in the purpose of being fixed to the mandible B1.

Second Embodiment

FIG. 4 is a perspective view illustrating a configuration of a second exemplary embodiment that maximizes the support performance of the supporting portion.

As shown in FIG. 4, a bone fragment-fixing device according to the second embodiment of the present invention has a configuration that is generally similar to the aforementioned configuration. Because a connecting portions 20 and a fixing portion 30 have the same configurations as the aforementioned configuration, detailed description thereof will not be provided, and a supporting portion 10 different from the aforementioned configuration will be mainly described.

As shown in FIG. 4, the supporting portion 10 according to the second embodiment is configured to support all the remaining areas except for the area of the cross-sectional area of the genioglossus muscle M connected on the inner surface of the bone fragment B2 in order to maximize the support performance of so as to Batochoso. That is, because the inducing portion 10b described in the first embodiment is not formed in the supporting portion 10, the supporting portion is made up of a ring-shaped member that forms a closed loop in which one side is not opened.

Third Embodiment

FIG. 5 is a perspective view illustrating a configuration of a third embodiment in which a switching portion is formed in the inducing portion of the supporting portion. As shown in FIG. 5, a bone fragment-fixing device according to the third embodiment of the present invention has generally the same configuration as that of the first embodiment.

However, the supporting portion 10 further includes a switching portion 10c that is capable of opening and closing the inducing portion 10b to be able to maximize the support performance of the supporting portion 10 after the genioglossus muscle M1 is induced to the receiving portion 10a.

The switching portion 10c is formed in a flat plate shape corresponding to the inducing portion 10b, and one side terminal end thereof is rotatably provided at one side terminal end of the opened supporting portion 10.

At this time, the switching portion 10c is formed relatively longer than the inducing portion 10b to easily close the opened inducing portion 10b and has a length by which the other terminal end of the switching portion 10c and the other side terminal end of the opened supporting portion 10 overlap each other at a predetermined interval.

Further, the longitudinal section of the switching portion 10c has a "U" shape so that the supporting portion 10 may be inserted into the switching portion 10c, and the switching portion 10c may be configured to be fixed to the supporting portion 10 through another locking device, after shielding the inducing portion 10b.

Fourth Embodiment

FIG. 6 is a perspective view illustrating a configuration of a fourth embodiment to which another embodiment of the switching portion is applied. As shown in FIG. 6, a bone fragment-fixing device according to the fourth embodiment of the present invention has generally the same configuration as that of the third embodiment.

The switching portion 10c is formed in a flat plate shape corresponding to the inducing portion 10b, and because the closing portion 10c needs to close the opened inducing portion 10b, the closing portion 10c is formed to be relatively longer than the inducing portion 10b and has a length by which the other side terminal end of the switching portion 10c and the other side terminal end of the opened supporting portion 10 overlap each other at a predetermined interval.

However, the switching portion 10c is provided to open and close the inducing portion 10b, while sliding along the radius of curvature of the supporting portion 10, rather than having a configuration in which the switching portion 10c is rotatably provided at one side terminal end of the opened supporting portion 10 and is opened and closed, while rotating.

In order to allow the switching portion 10c according to the present embodiment to stably slide along the supporting portion 10 and to prevent the switching portion 10c from being detached from the supporting portion 10, a guide groove is formed on any one side surface of the contact surface between the switching portion 10c and the supporting portion, and a protrusion to be inserted into the guide groove may be formed on the other side surface.

Further, as in the third embodiment, the switching portion 10c may be configured to be fixed to the supporting portion 10 through another locking device, after shielding the inducing portion 10b.

Fifth Embodiment

FIG. 7 is a perspective view illustrating a configuration of a sixth embodiment in which a switching member is formed in the inducing portion of the supporting portion.

As shown in FIG. 7, the bone fragment-fixing device according to the fifth embodiment of the present invention has a configuration that is generally similar to the aforementioned configurations. Because the supporting portion 10, the connecting portion 20 and the fixing portion 30 have the same configurations as those of the third embodiment and the fourth embodiment described above, the detailed description is will not be provided, and a switching portion 10c different from the aforementioned configuration will be mainly described.

The switching member 11 is formed so that it can be opened and closed, while being attached to and detached from the inducing portion 10b formed in the supporting part 10.

Because the switching member 11 has the same shape as the shapes of the switching portion 10c of the third embodiment and the fourth embodiment described above, the detailed description thereof will not be provided. However, unlike the third embodiment or the fourth embodiment, the switching member 11 is formed by an individual member in which one side is not fixed or does not slide.

The switching member 11 may include another fixing device such that its longitudinal section has a "U" shape, both terminal end portions of the supporting portion 10 are inserted into both terminal end portions of the switching portion 10c, and the switching member 11 is fixed by being coupled to both terminal end portions of the supporting portion 10 forming the inducing portion 10b after shielding the inducing portion 10b.

Further, the switching member 11 may be configured to include a separate auxiliary fixing portion 35 and an auxiliary connecting portion 25 such that the auxiliary fixing portion 35 is fixed to the mandible B1 to support the bone fragment B2 together with the supporting portion 10. Here, the auxiliary fixing portion 35 and the auxiliary connecting portion 25 provided in the switching member 110 have shapes that correspond to each of the fixing portion 30 and the connecting portion 20 provided in the supporting portion 10.

Sixth Embodiment

FIG. 8 is a perspective view illustrating a sixth embodiment in which the supporting portion is modified.

As shown in FIG. 8, a bone fragment-fixing device according to the sixth embodiment of the present invention has a configuration that is generally similar to the aforementioned configurations. Because the connecting portion 20 and the fixing portion 30 have the same configuration as the aforementioned configuration, the detailed description will not be provided, and the supporting portion 10 different from the aforementioned configuration will be mainly described.

The support portion 10 according to the sixth embodiment is configured to support a part of the bone fragment B2 by reducing the area of the supporting portion 10 as shown in FIG. 8. That is, the supporting portion 10 is formed in a flat plate shape capable of supporting a part of the frame of the bone fragment B2, and the inner surface being in contact with the genioglossus muscle M is formed with a gentle round to not stimulate the genioglossus muscle M.

Because the supporting device 10 according to the sixth embodiment supports the bone fragment B2 with a relatively small area, it is desirable to support the bone fragment B2 in several directions by using the two or more bone fragment-fixing devices and the bone fragment B2 in order to harmoniously and effectively support the bone fragment B2. In this way, when using a plurality of bone fragment-fixing devices, it is desirable to use the devices at equal intervals around the center axis of the bone fragment.

Seventh Embodiment

FIG. 9 is a perspective view illustrating an overall configuration of a bone fragment-fixing device according to a seventh embodiment of the present invention.

The bone fragment-fixing device of the seventh embodiment will be explained on the basis of a case of being used in a surgery for generally fixing the bone fragment rather than a case of being applied to the genioglossus muscle advancement surgery, unlike the first to sixth embodiments described above.

As shown in FIG. 9, the bone fragment-fixing device according to the seventh embodiment of the present invention has a configuration that is generally similar to the aforementioned configurations. Because the connecting portion 20 and the fixing portion 30 have the same configuration as the aforementioned configurations, the detailed description will not be provided, and the supporting portion 10 different from the aforementioned configurations will be mainly described.

Because there is no need to insert the genioglossus muscle into the supporting portion 10 of the seventh embodiment 10, a housing portion 10a or an inducing portion 10b are not formed, and the supporting portion 10 may be configured in a flat plate shape corresponding to the area of the bone fragment B2.

FIG. 9 shows, as an embodiment, a circular supporting portion 10 formed in accordance with the circular bone fragment B2, but the supporting portion 10 can be applied in various forms depending on the form of the bone fragment B2.

Eighth Embodiment

FIG. 10 is a perspective view illustrating a configuration of an eighth embodiment in which the supporting portion supports and fixes a part of the bone fragment.

As shown in FIG. 10, the bone fragment-fixing device according to the eighth embodiment of the present invention has a configuration that is generally similar to the aforementioned configurations. Because the connecting portion 20 and the fixing portion 30 have the same configuration as the aforementioned configurations, the detailed description will not be provided, and the supporting portion 10 different from the aforementioned configurations will be mainly described.

Although the supporting portion 10 preferably has the form that generally shields the overall inner area of the bone fragment B2 as in the seventh embodiment described above, it is also possible to adopt the form of supporting only a partial area of the bone fragment B2 as in the eighth embodiment.

As an embodiment, the supporting portion 10 can be provided in the flat plate shape that is formed in a semicircular shape to support a part of the bone fragment B2.

The form of the supporting portion 10 is variously applicable, and it is desirable to support the bone fragment B2 in various directions by utilizing the two or more bone fragment-fixing devices in order to harmoniously and effectively support the bone fragment B2.

Ninth Embodiment

FIG. 11 is a perspective view illustrating a configuration of a ninth embodiment in which a bone fragment-fixing device includes a plurality of connecting portions and fixing portions and, FIG. 12 is a perspective view illustrating a modified embodiment of the ninth embodiment.

As illustrated in FIGS. 11 and 12, the bone fragment-fixing device according to the ninth embodiment of the present invention has a configuration that is generally similar to the aforementioned configurations. Since the supporting portion 10 has the same configuration as the aforementioned configurations, the detailed description thereof will not be provided.

In the bone fragment-fixing device according to the ninth embodiment, a plurality of coupling portions 20 and fixing portions 30 are formed. At this time, the configuration and shape of the connecting portion 20 and the fixing portion 30 are the same as the aforementioned configurations.

As shown in FIG. 11, when applied to the bone fragment B2 of the typical form having a circular or polygonal cross-section, it is desirable to radially provide the arrangement of the connecting portion 20 and the fixing portion 30 so as to be spaced apart at equal intervals on the basis of the center axis of the bone fragment.

However, when applied to the bone fragment B2 of the a typical form, as shown in FIG. 12, the connecting portion 20 and the fixing portion 30 can be freely arranged depending on the form of the bone fragment B2 and the application of surgery for effective support function.

That is, it is possible to use the shape of the supporting portion 10, the number and the arrangement positions of the connecting portion 20 and the fixing portion 30, and the length H of the connecting portion 20 in various combinations, depending on the condition of the patient's bone subjected to the treatment using the bone fragment-fixing device according to the present invention, the contour and the shape of the bone fragment, the fixing method of the bone fragment and the like.

As in the ninth embodiment, the configuration in which a plurality of connecting portions 20 and fixing portions 30 are formed in the supporting portion 10 of the bone fragment-fixing device can also be applied to all of the aforementioned first to eighth embodiments, without being limited to the ninth embodiment.

Tenth Embodiment

FIG. 13 is a perspective view illustrating a configuration of a tenth embodiment in which the supporting portion includes a fixing member for being fastened to the bone fragment.

As shown in FIG. 13, the bone fragment-fixing device according to the tenth embodiment of the present invention has generally the same configuration as the first embodiment.

However, the bone fragment-fixing device according to the tenth embodiment is configured so that a coupling hole 13 formed in the supporting portion 10 in order to facilitate the surgery and more stably support the bone fragment, and the bolt 12 is inserted through the coupling hole 13 to fasten the bone fragment B2 and the supporting portion 10.

Similarly to the aforementioned fixing portion 30, the bolt 12 is made of titanium or various alloys for medical purpose, and a variety of coupling methods are applicable besides the bolt 12.

As in the tenth embodiment, the configuration in which the coupling hole 13 is formed in the supporting portion 10 of the bone fragment-fixing device can be applied to all of the first to ninth embodiments, without being limited to the tenth embodiment of the first embodiment described.

Configuration of Drill Assembly

FIG. 17 is a diagram illustrating the drill assembly for cutting the bone fragment according to the present invention, and FIG. 18 is a diagram illustrating a cross-section of the drill assembly for cutting the bone fragment according to the present invention.

As shown in FIG. 17, a drill assembly 40 according to the present invention is detachably connected to the drill, and blades for cutting the mandible B1 while rotating are formed to be arranged in a circular form.

As shown in FIG. 18, the first blade 41 is formed in a length L1 smaller than the thickness of the mandible B1, and the second blade 42 is formed at a length L2 longer than the thickness of the mandible B1.

Further, the second blade 42 is formed at a thickness T2 relatively thinner than the thickness T1 of the first serrations 41.

At this time, the outer diameters of the first blade 41 and the second blade 42 are formed equally.

Use Aspect and Function of Bone Fragment-Fixing Device

FIG. 14 is a diagram illustrating the cutting of the bone fragment, after performing the treatment of the genioglossus muscle advancement surgery, by using the bone fragment-fixing device according to an embodiment of the present invention, FIG. 15 is a sectional view illustrating a state in which the genioglossus muscle is pulled by treatment of the genioglossus muscle advancement surgery using the bone fragment-fixing device according to an embodiment of the present invention, and FIG. 16 is a sectional view illustrating a state of cutting the bone fragment protruding after treatment of the genioglossus muscle advancement surgery using the bone fragment-fixing device according to an embodiment of the present invention.

The bone fragment-fixing device according to the aforementioned first to tenth embodiments can be used for various treatments of the purposes of fixing the bone fragment B2 generated by cutting of the bone.

In particular, the bone fragment-fixing devices according to the first to sixth embodiments are device for surgery in a case where a muscle or the like is connected to the inside of the bone fragment, such as genioglossus muscle advancement surgery, and such a surgery will be mainly described.

The bone fragment B2 cut by the drill is pulled outward to expose the genioglossus muscle M connected to the back of the bone fragment B2 to the outside of the mandible B1.

Next, the bone fragment-fixing device is inserted into the cut bone fragment B2. The process of inserting the bone fragment-fixing device into the cut bone fragment B2 will be described in more detail as follows.

The genioglossus muscle M is inserted so as to be housed to the housing portion 10a formed in the supporting portion 10 through the inducing portion 10b of the supporting portion 10.

At this time, in the case of the bone fragment-fixing devices according to the fourth to sixth embodiments, it is possible to prevent the genioglossus muscle M from being detached from the housing portion 10a, while maximizing the performance of the supporting portion 10, by closing the switching portion 10c or connecting the switching member 11 after housing the genioglossus muscle M.

Further, as in the tenth embodiment, it is possible to more stably fix the bone fragment-fixing device to the bone fragment B2 by fixing the device with the fixing member.

Next, the bone fragment coupled to the bone fragment-fixing device is pushed into the hole in the mandible B1.

At this time, when the bone fragment B2 is inserted to a depth corresponding to the length H of the connecting portion of the bone fragment-fixing device 20, the fixing portion 30 comes into contact with the outer surface of the mandible B1 to prevent the bone fragment B2 from being further inserted. The state in which the genioglossus muscle M is pulled to the outside is maintained accordingly.

As described above, even when the supporting portion 10 is not fixed to the inside of the bone fragment B2 through the fixing member 12, because the genioglossus muscle M pulls the bone fragment B2 to the inside and the bone fragment-fixing device supports the bone fragment B2 from the inside, it is possible to obtain the effect in which the position of the bone fragment B2 is stably fixed.

Finally, by coupling the bolts 31 through the coupling hole 32 formed in the fixing portion 30 of the bone fragment-fixing device to fix the bone fragment-fixing device to the mandible B1, the surgery can be primarily completed.

Additionally, as shown in FIGS. 14 and 16, the bone fragment B2 protruding to the outer surface of the mandible B1 can be cut to correspond to the other surface of the mandible B1. Since the bone fragment B2 is supported on the inner side, it is possible to cut the protruding bone fragment B2 so that the existing form can be maintained without change in the outer surface shape of the mandible B1.

In the bone fragment fixing device of the present invention, unlike the conventional fixing device, because the fixing member enters only the fixing portion 30, the procedures and steps are simplified in the treatment, and it is possible to reduce the consumption of time and the patient's burden accordingly.

Further, since there is no external change in the patient's jaw after the treatment by cutting the protruding bone fragment B2, the device is effective in terms of beauty and there is an effect that can eliminate foreign body sensation which may be felt by a patient who received treatment and inconvenience in daily life.

As shown in FIG. 15, when performing the genioglossus muscle advancement surgery using the bone fragment-fixing device according to the present invention, the airway is extended while the genioglossus muscle M is pulled, which makes it possible to obtain the aimed snoring reduction effect.

Meanwhile, the bone fragment-fixing device of the present invention is universally applicable to a variety of surgeries, such as a genioplasty and a double jaw surgery, without being to the genioglossus muscle advancement surgery.

The bone fragment-fixing device according to the present invention can be freely deformed and applied, depending on the characteristics of the surgery operated by applying the bone fragment-fixing device and the patient's individual characteristics in addition to the first to tenth embodiments.

Further, when cutting the bone fragment B2, the bone fragment can be cut using a variety of methods and tools, and various forms of bone fragments B2 can be generated accordingly. Thus, the shape of the supporting portion 10 can also be variously applied to correspond to the form of the bone fragment B2.

In order to more stably fix the bone fragment-fixing device to the bone fragment, as shown in FIG. 13, it is also possible to couple the bone fragment B2 and the supporting portion 10 through a separate fixing member by forming the coupling hole 13 in the supporting portion 10.

In this way, coupling of the supporting portion 10 the bone fragment B2 through the fixing member may be selectively used, depending on the surgical method, the patient's condition and the like.

Use Aspect and Function of Drill Assembly

When the mandible B1 with the genioglossus muscle M connected thereto is cut using a drill, a circle saw is settled to the drill used for cutting the mandible B1 rotates, and the saw cuts the circular bone fragment B2 in the mandible B1 while rotating.

At this time, a lot of heat is generated due to the friction between the saw and the mandible B1.

To reduce such a frictional heat, it is desirable to cut the mandible B1 while replace other types of saws.

First, the mandible B1 is primarily cut using the first blade 41. At this time, since the length L1 of the first blade 41 is smaller than the thickness of the mandible B1, a circular groove is generated in the mandible B1 without completely cutting the bone fragment B2.

Next, when performing the secondary cutting by replacing the first blade with a second blade 42, since the length L2 of the second blade 42 is longer than the thickness of the mandible B1, the bone fragment B2 can be cut.

Since the outer diameter of the first blade and the outer diameter of the second blade are the same during such a process, when the second blade enters the circular groove generated in the primary cutting process, the size is consistent.

Further, since the thickness T2 of the second blade 42 is relatively smaller than the thickness T1 of the first serrations 41, it is possible to reduce the frictional heat, while being secondarily cut with a width smaller than the width of the circular groove generated in the primary cutting.

While preferred embodiment according to the present invention have been described above, it is obvious to those of ordinary skill in the art that the present invention can be embodied in other specific forms, without departing from its spirit or categories, in addition to the previously described embodiments. Accordingly, the above-described embodiments should be considered as being illustrative rather than being restrictive, and the present invention may be varied within the category of the appended claims and the scope of their equivalents, without being limited to the foregoing description accordingly.

The invention claimed is:

1. A bone fragment-fixing device comprising:
   a supporting portion adapted to support, on an inner side of a mandible, a bone fragment generated by cutting the mandible and that remains attached to a genioglossus muscle by an inner surface of the bone fragment, wherein the supporting portion is adapted to support the inner surface of the bone fragment without interfering with the genioglossus muscle during use;
   a housing portion forming part of the supporting portion and that is adapted to house the genioglossus muscle attached to the bone fragment during use;
   a connecting portion which is connected to one side of the supporting portion and is adapted to protrude to a height corresponding to an outer side of the mandible along a cut surface of the bone fragment during use; and
   a fixing portion connected to the connecting portion and formed in a shape so as to be adapted to correspond to the mandible around the bone fragment during use.

2. The bone fragment-fixing device of claim 1, wherein the supporting portion is formed with an inducing portion adapted to induce the genioglossus muscle to be housed in the housing portion during use.

3. The bone fragment-fixing device of claim 2, wherein the supporting portion further comprises a switching portion which opens and closes the inducing portion.

4. The bone fragment-fixing device of claim 2, further comprising:
   a switching member which includes an auxiliary supporting portion located in the inducing portion, the connecting portion and the fixing portion.

5. The bone fragment-fixing device of claim 2, wherein the supporting portion is semi-circular with a side opening, the side opening providing the inducing portion.

6. The bone fragment-fixing device of claim 1, wherein the supporting portion further includes a fixing member adapted to be fastened to the bone fragment during use.

7. The bone fragment-fixing device of claim 1, wherein the supporting portion is adapted to have an area smaller than an area of the bone fragment generated by cutting of the mandible during use.

* * * * *